United States Patent
Park et al.

(10) Patent No.: US 12,089,983 B2
(45) Date of Patent: Sep. 17, 2024

(54) X-RAY IMAGING DEVICE FOR DETECTING SHAKE

(71) Applicant: POSKOM CO., LTD., Gyeonggi-do (KR)

(72) Inventors: Jong Rae Park, Seoul (KR); Ki Bong Sung, Gyeonggi-do (KR)

(73) Assignee: POSKOM CO., LTD., Paju-si (KR)

( * ) Notice: Subject to any disclaimer, the term of this patent is extended or adjusted under 35 U.S.C. 154(b) by 184 days.

(21) Appl. No.: 17/565,433

(22) Filed: Dec. 29, 2021

(65) Prior Publication Data

US 2022/0323039 A1    Oct. 13, 2022

(30) Foreign Application Priority Data

Apr. 12, 2021    (KR) .................. 10-2021-0046921

(51) Int. Cl.
*A61B 6/00* (2024.01)
*A61B 6/46* (2024.01)
*A61B 6/58* (2024.01)

(52) U.S. Cl.
CPC ............ *A61B 6/586* (2013.01); *A61B 6/4405* (2013.01); *A61B 6/46* (2013.01)

(58) Field of Classification Search
None
See application file for complete search history.

(56) References Cited

U.S. PATENT DOCUMENTS

| 2012/0114099 A1* | 5/2012 | Yoshida | A61B 6/542 378/62 |
| 2017/0188443 A1* | 6/2017 | Nakahara | H05G 1/54 |
| 2018/0045660 A1* | 2/2018 | Yashima | G01N 23/083 |
| 2018/0333132 A1* | 11/2018 | Noda | A61B 6/581 |

FOREIGN PATENT DOCUMENTS

KR    10-2017-0125515    11/2017
KR    10-2018-0058902    6/2018

* cited by examiner

*Primary Examiner* — Hoon K Song
(74) *Attorney, Agent, or Firm* — Ladas & Parry, LLP (57) ABSTRACT

An X-ray imaging device may comprise: a radiation unit configured to preheat a filament and radiate an X-ray; a detection unit configured to detect shake of the radiation unit and generate information on the shake of the radiation unit; and a controller configured to determine a degree of the shake based on the information on the shake received from the detection unit and control an operation of the radiation unit depending on the determined degree of the shake. Therefore, the device can acquire a clear X-ray image without blur, and furthermore has effect in that unnecessary radiation exposure by re-photographing due to the blur of the X-ray image can be minimized.

4 Claims, 7 Drawing Sheets

X-RAY IMAGING DEVICE FOR DETECTING SHAKE

CROSS REFERENCE TO RELATED APPLICATION

This application claims priority from and benefit of Korean Patent Application No. 10-2021-0046921, filed on Apr. 12, 2021, which is hereby incorporated by reference for all purposes as if fully set forth herein.

TECHNICAL FIELD

The present disclosure relates to an X-ray imaging device, more specifically, an X-ray imaging device acquiring an X-ray image with a precise shape without blurring and minimizing unnecessary radiation exposure caused by re-photographing by detecting shake of a radiation unit during X-ray radiation, delaying X-ray radiation according to the detected shake, and initiating the X-ray radiation when the shake of the radiation unit is reduced,

BACKGROUND

In medical technical areas, X-ray imaging devices are widely used as means for acquiring an image of inside of human body.

The X-ray is called as a short-wavelength electromagnetic wave having a specific wavelength range and frequency range, and the X-ray imaging is radiography projecting the X-ray and displaying the inside of a photography object using high permeability of the X-ray.

As well known, X-rays accompany attenuation such as photoelectric effect or Compton scattering, depending on the material, density, and thickness of an object, while penetrating the object. Therefore, X-ray radiography displays a projected image for the inside of the object at a plane gray scale, based on an attenuation amount of X-rays which are accumulated while the X-rays penetrate the object. For this operation, a separate X-ray system is used.

Meanwhile, generally, such a X-ray imaging device is installed to be fixed, but, in addition to this fixed type X-ray imaging device, portable X-ray imaging devices which can easily carry are also widely used. Such a portable X-ray imaging device is used for the X-ray image photographing for animal, and its scope of application is extending to medical purposes or industrial purposes.

When photographing an X-ray image, the X-ray is radiated for a certain time period or a preset radiation exposure amount of the X-ray is radiated, and if shake occurs at the radiation unit radiating the X-ray during the X-ray radiation, the acquired X-ray image has blur, but to acquire a clear X-ray image without the blur, the shake at the radiation unit during the X-ray radiation should be prevented.

However, because people carry a portable X-ray imaging device with hands to perform the X-ray photographing, it is highly possible to occur the shake during the photographing, and therefore it is difficult of acquiring a clear X-ray image.

To solve the problems above, if necessary, the portable X-ray imaging device may be mounted to a holder or a mobile structure, but the shake can still occur during the fixation of the position of the radiation unit or in a process of photographing operations for moving and facing the X-ray imaging device to a photography target area, and significant time is required until the shake is completely stopped.

And, if re-photographing is required due to the shake of the radiation unit occurred during the X-ray imaging, there is a problem caused by necessary additional radiation exposure, and if the photographer does not recognize the shake of the radiation unit, the X-ray image with the blur caused by the shake can make a wrong diagnosis.

RELATED ART

Patent Documents (Patent Document 1) Korean Patent Application Publication No. 10-2018-0058902
(Patent Document 2) Korean Patent Application Publication No. 10-2017-0125515

SUMMARY

To solve the problems of conventional art described above, the purpose of the present disclosure is providing an X-ray imaging device detecting shake of a radiation unit, delaying X-ray radiation according to the detected shake, and initiating the X-ray radiation when the shake of the radiation unit is reduced.

Another purpose of the present disclosure is providing an X-ray imaging device in which a user can recognize whether shake occurs or not by outputting a warning alarm for notifying shake occurrence to the user if the shake is detected during X-ray radiation preparation or X-ray radiation.

According to an embodiment of the present disclosure, an X-ray imaging device may comprise: a radiation unit configured to preheat a filament and radiate an X-ray; a detection unit configured to detect shake of the radiation unit and generate information on the shake of the radiation unit; and a controller configured to determine a degree of the shake based on the information on the shake received from the detection unit and control an operation of the radiation unit depending on the determined degree of the shake.

In this embodiment, the X-ray imaging device may further comprise a manipulation unit configured to generate a radiation signal in response to manipulation of a user and provide the radiation signal to the controller, wherein the controller comprises a radiation controller configured to, if receiving the radiation signal, generate a radiation operation signal controlling the radiation unit to radiate the X-ray based on the degree of the shake.

Additionally, the radiation controller is configured to, if receiving the radiation signal, determine whether the degree of the shake is less than a first threshold, if the degree of the shake is less than the first threshold, generate the radiation operation signal, and, if the degree of the shake is equal to or more than the first threshold, halt generation of the radiation operation signal until the degree of the shake falls below the first threshold.

Further, the manipulation unit is configured to generate a preheat signal in response to the manipulation of the user and provide the preheat signal to the radiation controller, the radiation controller is configured to, if receiving the preheat signal, generate a preheat operation signal controlling to preheat a filament by the radiation unit, and if the providing of the preheat signal by the manipulation unit is halted or if time of halting generation of the radiation operation signal exceeds a reference time, generate a preheat halt signal controlling to halt preheat of the filament performed by the radiation unit.

In addition, the X-ray imaging device further comprises a warning alarm output unit configured to output a warning alarm, and the controller comprises an alarm controller configured to, if the degree of the shake is equal to or more than a second threshold, generate an alarm output signal so that the warning alarm output unit outputs the warning alarm, Additionally, the alarm controller is configured to, if an average of the degree of the shake determined while the radiation unit radiates the X-ray is equal to or more than a third threshold, generate the alarm output signal.

Further, the controller further comprises a position determination unit configured to determine change in a position of the radiation unit based on information of a movement direction of the radiation unit and information of a movement distance of the radiation unit included in the information on the shake of the radiation unit, and the alarm controller is configured to generate the alarm output signal based on the change in the position determined by the position determination unit.

In addition, the alarm controller is configured to, if a separation distance or straight distance between a position of the radiation unit where X-ray radiation starts and a position of the radiation unit where the X-ray radiation ends is equal to or more than a reference distance, generate the alarm output signal.

According to some exemplary embodiment of the present embodiment, by detecting shake of a radiation unit, delaying X-ray radiation according to the detected shake, and initiating the X-ray radiation when the shake of the radiation unit is reduced, a clear X-ray image without blur can be acquired and unnecessary radiation exposure caused by re-photographing due to the blur of the X-ray image can be minimized.

Additionally, according to certain embodiments of the present disclosure, by outputting a warning alarm for notifying shake occurrence to a user if shake is detected during X-ray radiation preparation or X-ray radiation, misdiagnosis as difference causes (diseases and so on) due to the shake can be prevented when examining the acquired X-ray image.

DETAILED DESCRIPTION OF EMBODIMENTS

The technical terms used in the present disclosure are only for the purpose of describing exemplary embodiments, and they are not intended to limit the present invention. Also, unless otherwise defined, all technical terms used herein should be construed as having the same meaning as commonly understood by those skilled in the art, and should not be interpreted as being excessively inclusive or excessively restrictive. In addition, when a technical term used herein is an erroneous technical term that does not accurately represent the idea of the present invention, it should be understood as replacing the term by a technical term which can be properly understood by those skilled in the art.

Further, singular expressions used in the present specification include plural expressions unless they have definitely opposite meanings. In the present application, it shall not be construed that terms, such as "including" or "comprising", various constituent elements or steps described in the specification need to be all essentially included, and it shall be construed that some constituent elements or steps among the various constituent elements or steps may be omitted, or additional constituent elements or steps may be further included.

Also, it should be noted that the accompanying drawings are merely illustrated to easily explain the spirit of the invention, and therefore, they should not be construed to limit the spirit of the invention by the accompanying drawings.

Hereinafter, with reference to the enclosed drawings, an X-ray imaging device according to an embodiment of the present disclosure is described in detail.

Figure 1:
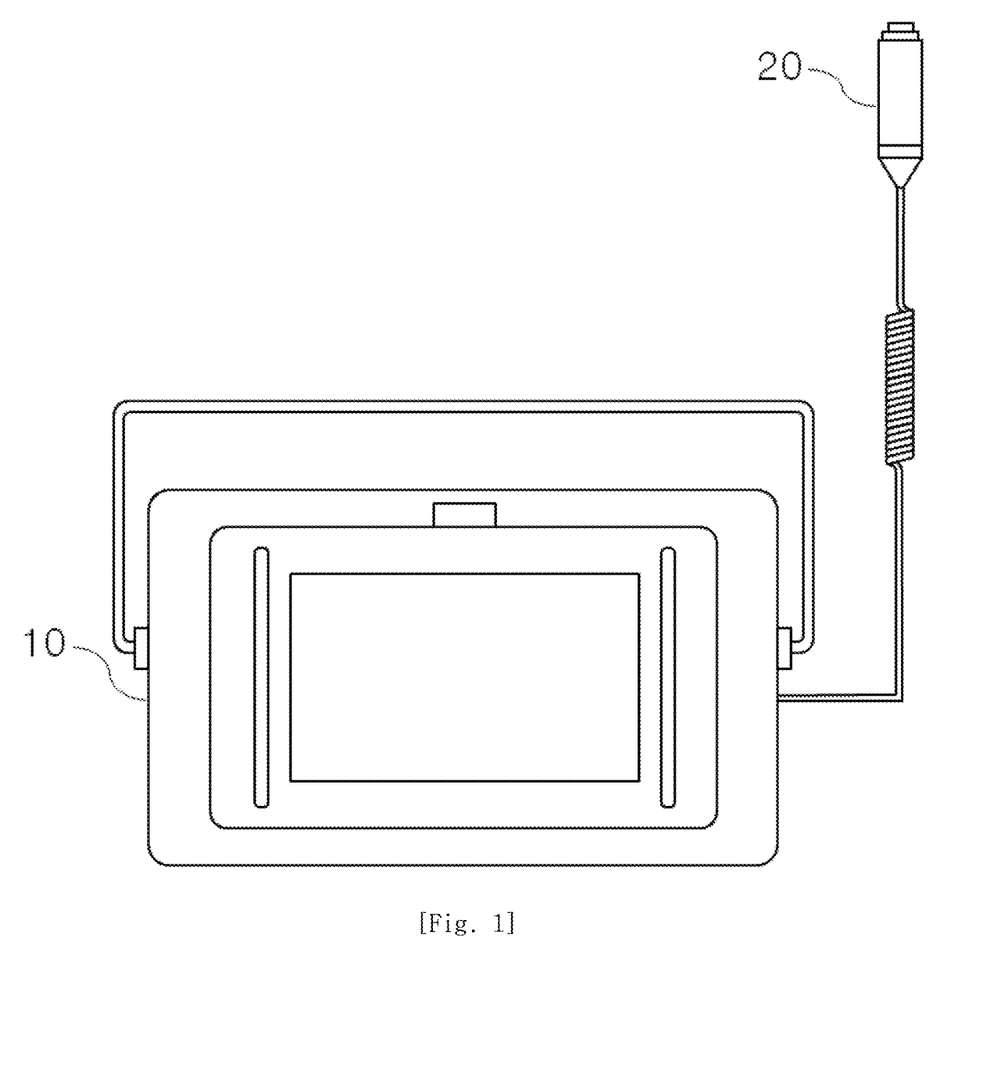
FIG. 1 is a schematic diagram for illustrating an X-ray imaging device according to an embodiment of the present disclosure.

FIG. 1 is a schematic diagram for illustrating an X-ray imaging device according to an embodiment of the present disclosure.

The x-ray imaging device according to the present disclosure is configured to comprise a main body for generating an X-ray and radiating the X-ray to a photography object and a manipulation unit (20) for inputting a user command.

The main body (10) can have various configurations for generating and radiating the X-ray. The manipulation unit (20) comprises a first button for generating a preheat signal according to a user manipulation and a second button for generating a radiation signal according to a user manipulation, and by providing the preheat signal and the radiation signal to the main body (10), the main body (10) can perform filament present for X-ray radiation or the X-ray radiation.

Here, the manipulation unit (20) can be wired or wirelessly connected to the main body (10) to improve easiness of the user's manipulation. In the following descriptions, the manipulation unit (20) is illustrated as being separated from the main body (10), but depending on fields to which the present disclosure is applied the manipulation unit (20) the manipulation unit (20) may be formed at one side of the main body (10) and this embodiment is within the scope of the present disclosure.

The main body (10) of the X-ray imaging device according to an embodiment of the present disclosure is manufactured as a portable type to be compact and light so that it can be easily moved to a necessary space to X-ray human or animal, and, in a state that the user holds the main body (10) of the X-ray imaging device with hand when X-raying, the user maintains fixation to a position and performs the X-ray imaging to photograph an intended part of a photography object, or, after mounting the main body (10) of the X-ray imaging device to a holder, moves the position to an intended part of a photography object and photographs it.

In order to acquire a clear and precise X-ray image, the main body (10) of the X-ray imaging device should not be shaken during the radiation of the X-ray to the photography object. However, when the user holds the main body (10) of the X-ray imaging device with hands, the shaken of the main body (10) of the X-ray imaging device may happen during photographing, and when photographing in a state that the main body (10) of the X-ray imaging device is mounted to the holder, the shaken of the main body (10) of the X-ray imaging device may happens due to the shaken of the holder for a certain time period after the main body (10) of the X-ray imaging device mounted to the holder is moved to an intended photography part.

During the process of X-raying, the X-ray imaging device according to an embodiment of the present disclosure, if detecting the shaken of the main body (10), delays or stops the X-ray radiation in order to acquire a precise and clear X-ray image without blur, and if the shaken more than a threshold is detected during the X-ray radiation or the radiation preparation, outputs an warning alarm to notify occurrence of shake to the user so that the user can recognize the occurrence of the shake.

In the following descriptions, detailed configurations of the present disclosure of photographing a clear X-ray image without blur by detecting shake in the X-ray imaging device are provided.

Figure 2:
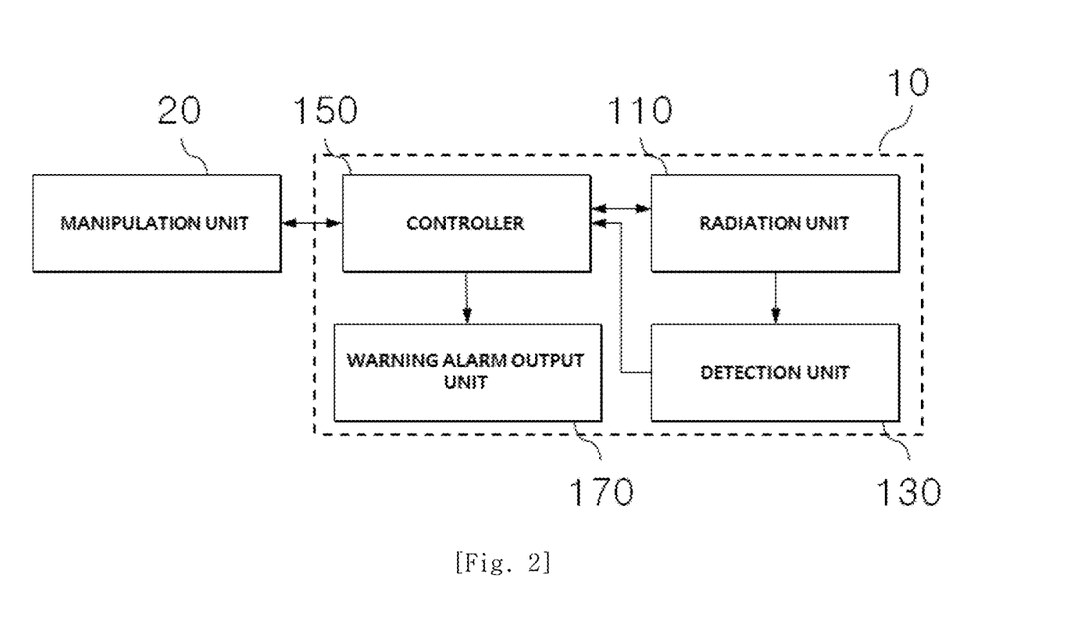
FIG. 2 is a block diagram for illustrating an X-ray imaging device according to an embodiment of the present disclosure.

FIG. 2 is a block diagram for illustrating an X-ray imaging device according to an embodiment of the present disclosure.

The X-ray imaging device according to an embodiment of the present disclosure may be configured to comprise the main body (10) and the manipulation unit (20), and the main body (10) may comprise a radiation unit (110) configured to generate X-ray and radiate the generated X-ray, a detection unit (130) configured to detect shake of the radiation unit (110), a controller (150) configured to control operation of the radiation unit (110) based on the signal provided from the manipulation unit (20) and the shake of the radiation unit (110). Preferably, the radiation unit (110), the detection unit (130) and the controller (150) may be disposed inside a housing of the main body (10) of the X-ray imaging device or outside of the housing of the main body (10).

The radiation unit (110) preheats a filament and radiates X-ray. Specifically, the radiation unit (110) operates according to various signals provided from the controller (150), if receiving a preheat operation signal from the controller (150), the radiation unit (110) initiates the preheat of the filament, if receiving a preheat halt signal, stops the operation of the filament preheat, and may initiate the X-ray radiation if receiving a radiation operation signal and stop the X-ray radiation if receiving a radiation halt signal.

The detection unit or sensor (130) is configured to generate shake information by detecting shake of the radiation unit (110). Preferably, the detection unit (130) can generate the shake information by detecting the shake of the main body (10) of the X-ray imaging device to which the radiation unit (110) is mounted, and provide the generated shake information to the controller (150).

The controller (150) can determine a degree of the shake happening in the radiation unit (110) based on the shake information provided from the detection unit (130). Here, the degree of the shake may mean a degree of acceleration or amplitude of the movement of the radiation unit (110).

The controller (150) basically controls the radiation unit (110) based on the preheat signal and the radiation signal provided from the manipulation unit (20). Specifically, if receiving a preheat signal from the manipulation unit (20), the controller (150) generates the preheat operation signal, and if the transmission of the preheat signal is discontinued, the controller (150) generates the preheat halt signal. And, if receiving a radiation signal from the manipulation unit (20), the controller (150) generates the radiational operation signal, and if the radiation signal is not provided or the X-ray radiation for a set time period (or a set radiation exposure amount) is completed, the controller (150) can generate the radiation halt signal. Depending on fields to which the present disclosure is applied, if receiving the preheat signal, the controller (150) generates the preheat operation signal and preheats the filament of the manipulation unit (20), and if the supply of the preheat signal is discontinued, the preheat of the filament of the manipulation unit (20) can be halted immediately without generating a preheat halt signal. Accordingly, the filament of the manipulation unit (20) can be preheated by the preheat operation signal only and if there is no heat operation signal, the preheat can be halted.

At that time, in order to minimize the blur of the X-ray image caused by the shake of the radiation unit (110) and minimize unnecessary radiation exposure, the controller (150) can control the operation of the radiation unit (110).

Specifically, the controller (110) can delay in generating a radiation operation signal when shake more than a certain degree exists even if a radiation signal is received from the manipulation unit (20), and more detailed descriptions regarding the controlling of the radiation unit (110) performed by the controller (150) based on the shake degree will be provided below by referring to FIG. 4.

Meanwhile, the X-ray imaging device according to an embodiment of the present disclosure, when the shake of the radiation unit (110) happens, outputs a warning alarm so that the user can recognize the shape of the radiation unit (110).

For this, the X-ray imaging device according to an embodiment of the present disclosure, may further comprise a warning alarm output unit (170) configured to output a warning alarm, and the controller (150) is configured to control the operation of the warning alarm output unit (170) according to the shake degree of the radiation unit.

Specifically, the warning alarm output unit (170) can output a warning alarm in a form of text, light or sound, and output means for outputting text, light or sound can be mounted to the main body (10) of the X-ray imaging device or be provided separated from the main body (10).

If the controller (150) determines that the shake more than a certain degree is happened at the radiation unit (110), the controller (150) can generate an alarm output signal. The generated alarm output signal is provided to the warning alarm output unit (170), the warning alarm output unit (170) which receives the alarm output signal outputs a warning alarm to the user so that the occurrence of the shake at the radiation unit (110) can be recognized by the user. Like this, the warning alarm is outputted in real time when the shake of the radiation unit (110) occurs during the filament preheat or the X-ray radiation to notify the user the shake of the radiation unit (110) in real time, or the warning alarm is outputted after completing the X-ray photography so that the occurrence of the shake during the photographing of the acquired X-ray image can be notified to the user.

Figure 3:
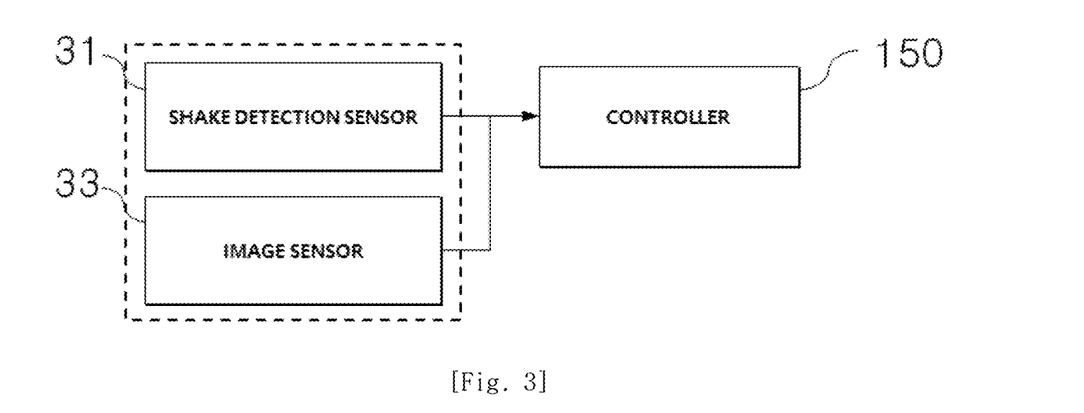
FIG. 3 is a block diagram for illustrating a detection unit according to an embodiment of the present disclosure.

FIG. 3 is a block diagram for illustrating a detection unit according to an embodiment of the present disclosure.

In the following descriptions, detailed configurations of the detection unit or sensor (130) according to an embodiment of the present disclosure are described by referring FIG. 3.

The detection unit (130) may be configured to comprise a shake detection sensor (131) configured to detect shake of the radiation unit (110).

The shake detection sensor (131) is arranged to the main body (10) and is configured to detect the shake of the radiation unit (110) through the shake of the main body (10).

Specifically, the shake detection sensor (131) can generate shake information comprising inclination information, acceleration information, movement direction information, and movement distance information of the radiation unit (110) and so on by detecting inclination, acceleration, a movement direction, and a movement distance of the radiation unit (110) and so on, and provide the generated shake information to the controller (150). Here, the shake detection sensor (131) may be implemented as a motion sensor or gyro sensor and so on.

Meanwhile, when the shake of the radiation unit (110) occurs during the X-ray photography, the blur of the X-ray image may exist, but when the photography object is moved during the X-ray photography, the blur of the X-ray image can exist too. Accordingly, if only the shake of the radiation unit (110) is detected, the blur caused by the movement of the photography object cannot be responded, and therefore, in order to respond to the blur caused by the movement of the photography object, the movement of the photography objection also needs to be detected. For this, the detection unit (130) according to the present disclosure may further include an image sensor (133).

The image sensor (133) may acquire an object image and provide the acquired object to the controller (150). Accordingly, the image sensor (133) can generate shake information in a form of an object image and provide it to the controller (150).

In the present embodiment, the image sensor (133) may be provided as a separate device from the main body (2) of the X-ray imaging device, but this embodiment may have disadvantage that the user needs to adjust a photography angle of the image sensor (133) to acquire the object image every time when X-ray photographing.

To solve this problem, the image sensor (133) may be mounted to the main body (20) of the X-ray imaging device, and, specifically, the image sensor (133) is arranged to face a direction the same as a direction of radiating X-ray from the radiation unit (110) to acquire an image of the photography object. Preferably, the image sensor (133) is arranged at the same side as the radiation unit (110) to acquire the image of the photography object positioned in a direction of radiating the X-ray from the radiation unit (110). Like this, when the image sensor (133) is disposed at the same side as the radiation unit (110), if the radiation unit (110) faces the photography object for X-ray photographing, the photography angle of the image sensor (133) also faces the photography object, and therefore the object image can be acquired without an additional process for adjusting the photography angle of the image sensor (133).

The object image acquired by the image sensor (133) is provided to the controller (150), and the controller (150) determines the shake of the object based on the object image provided by the image sensor (133). Specifically, the controller (150) can generate a virtual reference area at a center portion of the provided object image, and determine the RGB value of pixels corresponding to the generated reference area. The controller (150) repeatedly performs the RGB value determination on the continuously provided object images, and determine the degree of the shake based on the rate of change in the RGB values of the object images.

In this embodiment, when the image sensor (133) is mounted to the main body (10) as described above, the shake determined based on the object image may be the shake (movement) of the photography object, but it may be the shake of the radiation unit (110). This is because the shake of the object image exists when the photography object is moved, but the shake of the object image may exist when the radiation unit (110) mounted to the main body (10) is shaken. However, a process that the user responds to a case where the photography object is moved and a process that the user responds another case where the radiation unit (110) is shaken may be different from each other. For example, when the photography object is moved, the photography object needs to be fixed not to move, but when the radiation unit (110) is shaken, the radiation unit (110) needs to be fixed not to be shaken.

Accordingly, when determining a degree of the shake based on the provided object image, the controller (150) determines whether a shook subject is the radiation unit (110) or the photography object, and, preferably, the warning alarm output unit (170) differently outputs each of a first warning alarm of a case in which the radiation unit (120) is shaken and a second warning alarm of a case in which the photography object is moved.

Specifically, when the degree of the shake determined based on the shake information provided from the shake detection sensor (131) is more than a predetermined value, the controller (150) determines that the shook subject is the radiation unit (110) regardless of the degree of the shake determined based on the object image. However, when the degree of the shake determined based on the shake information provided from the shake detection sensor (131) is less than a predetermined value and the degree of the shake determined based on the object image provided at the same time is greater than a predetermined value, the controller (150) determines that the shook subject is the photography object.

By the processes described above, the controller (150) can determine the degree of the shake as well as the shook subject, and can add information regarding the shook subject to the generated shake degree information. And, when generating the alarm output signal, an alarm output signal distinguished depending on the shook subject information can be generated.

Specifically, the controller (150) generates a first alarm output signal when a shaken subject is the radiation unit (110) because the degree of the shake is determined to be more than a predetermined value, and generates a second alarm output signal when the shaken subject is the photography object. And, the warning alarm output unit (170) can output warning alarms different from each other when outputting the first alarm output signal and the second alarm output signal, respectively.

By the warning alarm outputs distinguished from each other, the user can distinguish and distinctively recognize that the occurrence cause of the warning alarm is the shake of the radiation unit (110) or the shake of the photography object, and take proper action depending on the occurrence cause of the warning alarm.

Figure 4:
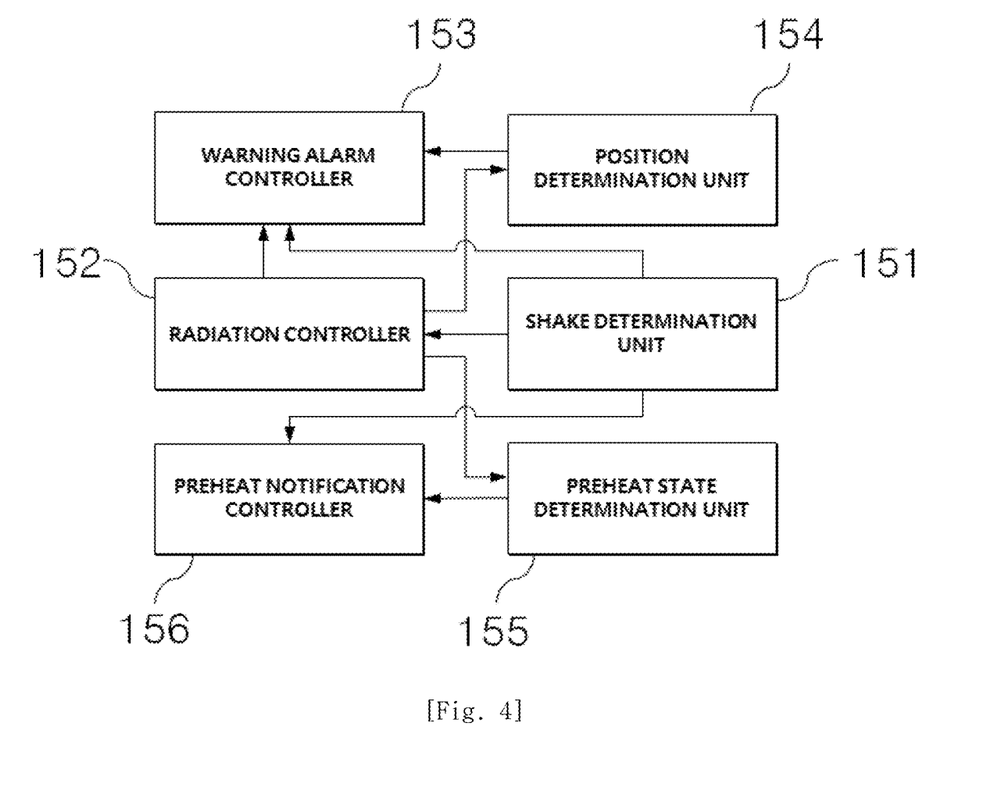
FIG. 4 is a block diagram of a controller according to an embodiment of the present disclosure.
Figure 5:
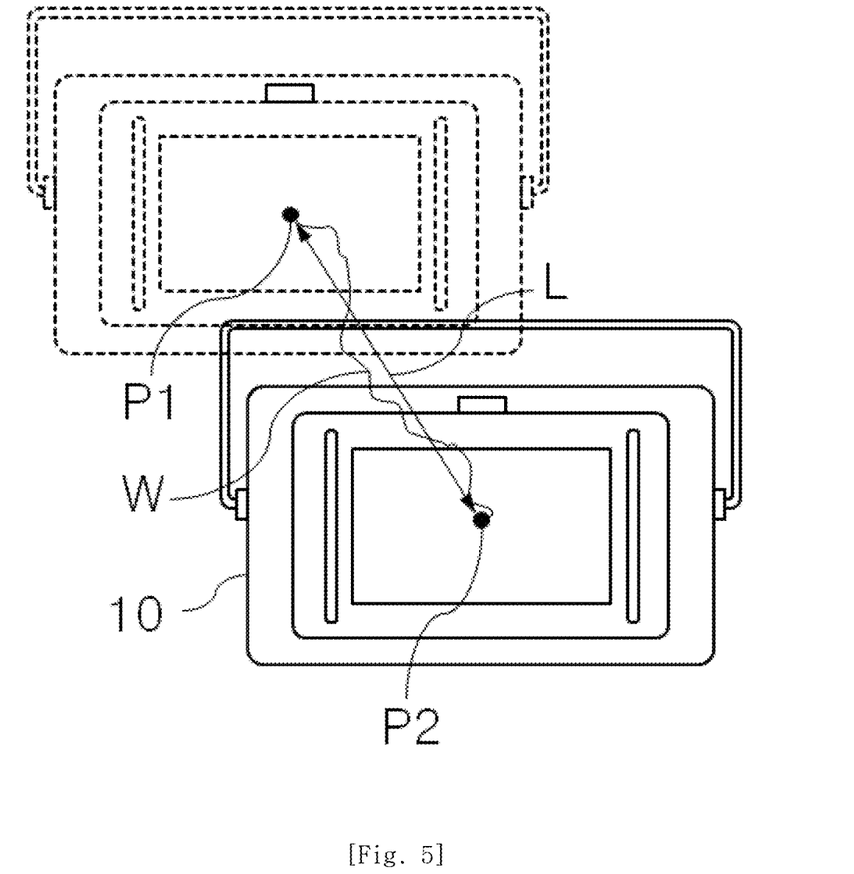
FIG. 5 is a figure for illustrating an example of position change of a main body during X-ray photographing according to an embodiment of the present disclosure.

FIG. 4 is a block diagram of a controller according to an embodiment of the present disclosure, and FIG. 5 is a figure for illustrating an example of position changing of a main body during X-ray photographing according to an embodiment of the present disclosure.

In the following description, detailed configurations of the controller (150) are described by referring FIG. 4.

As described above, the controller (150) determines the degree of the shake based on the provided shake information, and controls the operation of the radiation unit (110) based on the determined degree of the shake.

For this, the controller (150) may comprise a shake degree determination unit (151) configured to determine the degree of the shake of the radiation unit (110), and a radiation controller (152) configured to various signals to control the operation of the radiation unit (110).

The shake degree determination unit (151) determines the degree of shake based on the shake information provided from the determination unit (130) in real time, and can generate shake degree information depending on the determination result.

As described above, the controller (150) can generate a preheat operation signal, a preheat halt signal, a radiation operation signal and a radiation halt signal for controlling the operation of the radiation unit (110), and like this, various signals for controlling the operation of the radiation unit (110) can be generated by the radiation controller (152).

The radiation controller (152) generates a radiation operation signal when receiving a radiation signal from the manipulation unit (20), but, when the occurrence of the shake more than a predetermined value at the radiation unit (110) or the photography object, the generation of the radiation operation signal can be delayed even if receiving the radiation signal from the manipulation unit (20).

Specifically, when receiving the radiation signal from the manipulation signal (20), the radiation controller (152) compares the degree of the shake determined by the shake determination unit (151) in real time with a first threshold, and determines whether the degree of the shake determined in real time is less than the first threshold. If the degree of the shake is less than the first threshold, the radiation controller (152) immediately generates a radiation operation signal and provides it to the radiation unit (110). However, if the degree of the shake determined in real time is equal to or more than the first threshold, the generation of the radiation operation signal can be postponed until the degree of the shake falls less than the first threshold.

Accordingly, the X-ray imaging device according to the present embodiment can delay the X-ray radiation while the radiation unit (110) or the photography object is being shaken even though the user manipulates for the X-ray radiation, and radiates the X-ray at the time when the shake of the radiation unit (110) or the photography object is reduced, and therefore can acquire a clear X-ray image without blur, and furthermore has a technical effect that unnecessary radiation exposure by re-photographing due to the X-ray image blur can be minimized.

Preferably, when a generation delay time of the radiation operation signal exceeds a reference time, the radiation controller (152) can generate a preheat halt signal regardless of whether a preheat signal is received from the manipulation unit (20). Specifically, when the generation of the radiation operation signal is delayed, the radiation controller (152) counts delay time, and when the counted delay time exceeds the reference time, the radiation controller (152) can generate a preheat halt signal. This is for preventing overly preheating a filament by prolonging the X-ray radiation delay time because the degree of the shake continuously fails to fall below the first threshold during the delay in generating the radiation operation signal.

Additionally, depending on fields to which the present disclosure applies, the radiation controller (152) continuously monitors the degree of the shake of the radiation unit (110) in real time, and, when the degree of the shake of the radiation unit (110) exceeds a preset level during the X-ray radiation, the radiation controller (152) provides a radiation halt signal to the radiation unit (110) to stop the X-ray radiation even when the preset X-ray radiation time does not pass or even before the preset X-radiation exposure amount is reached.

Meanwhile, as described above, the controller (150) controls the operation of the warning alarm output unit (170) to output a warning alarm regarding the shake, and, for this, the controller (150) may further comprise an alarm controller (153) configured to generate an alarm output signal.

The alarm controller (153) compares a real time shake degree determined during the filament preheat and the X-ray radiation of the radiation unit (110) with a second threshold, and determines whether the real time shake degree is equal to or more than the second threshold. When the real time shake degree is equal to or more than the second threshold, the radiation controller (152) generates an alarm output signal and provides the generated alarm output signal to the warning alarm output unit (170). Here, the second threshold may be identical to or different from the first threshold.

In that time, the comparison between the second threshold and the real time shake degree can be performed by the alarm controller (153) from time of starting the filament preheat to time of completing the X-ray radiation, and the alarm controller (153) receives the preheat operation signal and the radiation halt signal from the radiation controller (152) and determines the time of starting the filament preheat and the time of completing the X-ray radiation based on those signals.

Accordingly, the X-ray imaging device according to the present embodiment notifies in real time the shake of the radiation unit (110) or the photography object occurred during the filament preheat and the X-ray radiation to the user. In this time, the user can take different actions depending on time of outputting a warning alarm. Specifically, if the warning alarm is outputted before the X-ray radiation (or during the filament preheat), the user can fix the position of the radiation unit (110) or the photography object not to be shaken or manipulate a second button at the time in which the shake frequently occurs thereby acquiring a clear and precise X-ray image. And, when the warning alarm is outputted during the X-ray radiation, the user immediately stops the X-ray radiation to halt the X-ray photographing in which it is expected that the X-ray image has a blur, thereby minimizing the unnecessary X-ray exposure, or continues the X-ray imaging process without stopping the X-ray radiation and examines the X-ray image by considering that the acquired X-ray image has the blur.

Meanwhile, when the shake continues for a relatively long time during the X-ray radiation even though the radiation unit (110) or the photography object is not temporarily largely shaken, the blur may occur in the acquired X-ray image. Accordingly, the alarm controller (153) may generate a warning alarm signal based on an average of the degree of the shake during the radiation of the X-ray by the radiation unit (110).

Specifically, the alarm controller (153) determines whether the X-ray is radiated by the radiation unit (100) and calculates the average of the degree of the shake during the X-ray radiation based on the radiation operation signal and the radiation halt signal provided from the radiation controller (152). The alarm controller (153) compares the calculated average with a third threshold, and, if the calculated average is equal to or more than the third threshold, the alarm controller (153) can generate a warning alarm output signal. Here, the third threshold may be identical to or different from the first threshold or the second threshold.

Additionally, if the change in the position of the radiation unit (110) from the X-ray radiation start time to the X-ray radiation end time is large even though the shake of the radiation unit (110) occurred during the X-ray radiation is small, the blur may occur in the acquired X-ray image.

When FIG. 5 is explained as an example, if the main body (10) to which the radiation unit (110) is mounted is slowly moved downwardly so that the position (P2) in which the X-ray radiation is completed is largely lowered than the position (P1) in which the X-ray radiation is started even though the radiation unit (110) is not largely shaken during the X-ray radiation, the blur occurs in the acquired X-ray image. Accordingly, if the change in the position of the radiation unit (110) during the X-ray radiation is large even though the shake of the radiation unit (110) is relatively small, the alarm controller (150) can generate the alarm output signal so that the user can be notified that the blur exists in the X-ray image.

For this, the controller (150) comprises a position determination unit (154) configured to determine the change in the position of the radiation unit (110), and the alarm controller (150) can generate the alarm output signal based on the change in the position of the radiation unit (110) determined by the position determination unit (154).

The position determination unit (154) can determine the change in the position of the radiation unit (110) based on the movement direction information and the movement distance information of the radiation unit (110) comprised in the shake information provided from the determination unit (130).

Specifically, the position determination unit (154) is configured to receive the radiation operation signal and the radiation halt signal from the radiation controller (152), and if receiving the radiation operation signal, the position determination unit (154) generates a virtual reference position and the position (P1) where the X-ray radiation of the radiation unit is started can be set as the virtual reference position. And, the position determination unit (154) can generate a movement path (W) from the position (P1) where the X-ray radiation of the radiation unit is started with consideration of the movement direction and the movement distance of the radiation unit (110) from time of receiving the radiation operation signal to time of receiving the radiation halt signal. At that time, the position determination unit (154) sets the position (P2) where the X-ray radiation of the radiation unit is completed as the end of the movement path.

The information on the position (P1) at the time of starting the X-ray radiation of the radiation unit and the information on the position (P2) at the time of completing the X-ray radiation of the radiation unit determined through the process described above can be provided to the alarm controller (153). The alarm controller (153) determines a separation distance or straight distance (L) from the position (P1) at the time of starting the X-ray radiation of the radiation unit to the position (P2) at the time of completing the X-ray radiation of the radiation unit, and compares the determined separation or straight distance with a reference distance and generates an alarm output signal if the separation or straight distance is equal to or greater than the reference distance.

Therefore, the X-ray imaging device can predict X-ray image blur occurrence according to the change in the position of the radiation unit (110) during the x-ray radiation and notify it to the user even though the large shake does not occur in the radiation unit (110) during the radiation of the X-ray.

Meanwhile, as described above, the filament preheat more than a certain degree is required for the X-ray radiation. Accordingly, the user presses a first button, and then after checking that the filament preheat more than the certain degree is completed, the user presses a second button. For this process, the manipulation unit (20) can have a preheat completion notification means so that the user can be notified that the filament preheat is completed. And, as illustrated in FIG. 4, the controller (150) can include a preheat state determination unit (155) configured to determine a preheat state of the filament, and a preheat notification controller (156) configured to generate a preheat notification signal for controlling the operation of the preheat completion notification.

The preheat state determination unit (155) is configured to receive the preheat operation signal from the radiation controller (152), and, after a set time passes from time of receiving the preheat operation signal, determine that the preheat is completed. Here, the preheat completion means a state that the filament preheat is performed for a time period more than a predetermined value so that the X-ray radiation can be performed or a state that the X-ray more than a predetermined radiation exposure amount can be radiated, and the threshold for the preheat may be changed depending on a predetermined X-ray radiation time period or X-ray exposure amount.

When the preheat state determination unit (155) determines that the preheat of the filament is completed, the preheat notification controller (156) generates the preheat notification signal and provides the generated preheat notification signal to a preheat completeness notification means.

Preferably, when the preheat notification signal is generated, the preheat notification controller (156) can delay the generation of the preheat notification signal based on the degree of the shake of the radiation unit (110) or the photography object. Specifically, if determining that the preheat of the filament is completed, the preheat notification controller (156) compares a real time degree of the shake of the radiation unit (10) or the photograph object with a first threshold, and determines whether the real time degree of the shake is equal to or more than the first threshold. If the degree of the shake is less than the first threshold, the preheat notification signal is generated immediately and the generated preheat notification signal is provided to the preheat completion notification means, but if the real time degree of the shake is equal to or more than first threshold, the generation of the preheat notification signal can be delayed. Accordingly, when the radiation controller (152) delays the generation of the radiation operation signal while the degree of the shake is equal to or more than first threshold, the preheat notification controller (156) can also delay the generation of the preheat notification signal and therefore the preheat completion notification means can delay in notifying the preheat completion. Accordingly, even though the preheat of the filament is completed, by not generating the preheat completion notification while the X-ray radiation is delayed due to the shake of the radiation unit (110) or the photography object even when the user manipulates the second button, the user does not need to perform meaningless manipulation of the second button caused by the preheat completion notification.

Meanwhile, the preheat completion notification means can output light or sound or generate vibration if receiving the preheat notification signal from the preheat notification controller (156). Specifically, the preheat completion notification means may comprise at least one of a LED module notifying completion of the preheat by outputting light, a vibration module completion of the preheat by generating vibration, and a speaker module notifying completion of the preheat by outputting sound.

The preheat completion notification means receiving the preheat notification signal can notify, by light or vibration or sound, the user that the preheat is completed and the X-ray radiation is ready.

When the LED module is included as the preheat completion notification means, the LED module can be mounted to the second button. When the LED module mounted to the second button outputs light, it looks like that the second button emits the light, and the user who sees the second button emitting the light can recognize that the second button is in a state that the second button is pressable (or a state that the filament preheat is ready).

When the vibration module or the speaker module is installed, the preheat notification controller (156) can provide the generated preheat notification signal to not only the LED module but also the vibration module or the speaker module, and when the filament preheat is completed, the light is emitted from the LED and, at the same time, the vibration module generates the vibration or the speaker module outputs the sound. Like this, when the LED module as well as the vibration module or the speaker module are included as the preheat completion notification means, the user can recognize the completion of the filament preheat through touch or hearing in addition to sight.

Figure 6:
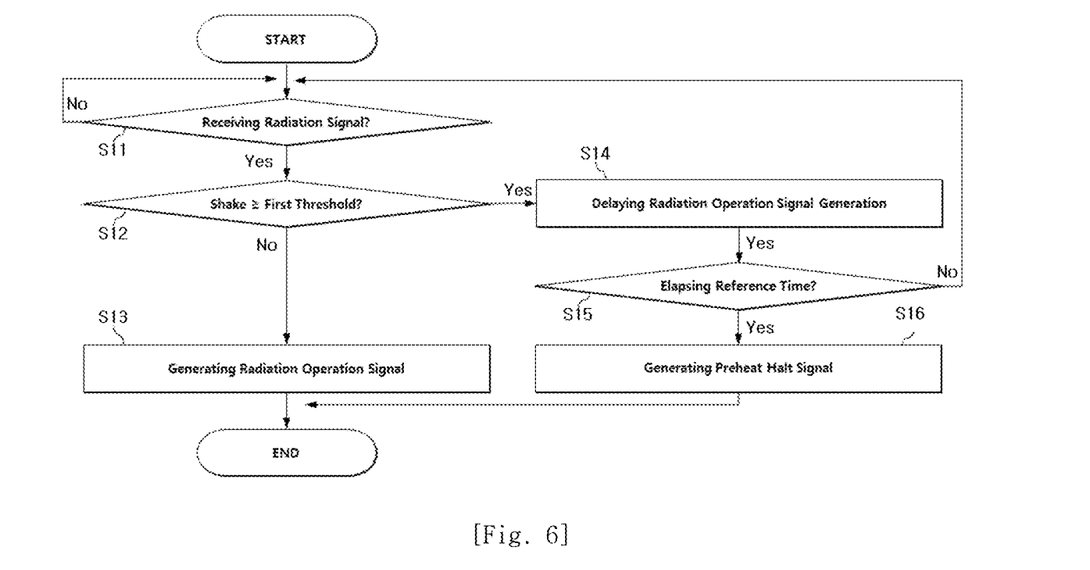
FIG. 6 is a flow chart for illustrating a control process of a radiation controller according to an embodiment of the present disclosure.

FIG. 6 is a flow chart for illustrating a control process of a radiation controller according to an embodiment of the present disclosure.

In the following descriptions, steps of generating one or more signals for controlling the radiation unit (110) by the radiation controller (152) are described referring to FIG. 6.

Firstly, the radiation controller (152) can determine whether a radiation signal is provided from the manipulation unit (20) (S11). If the radiation signal is not provided (S11—N), the radiation controller (152) stands by until receiving the radiation signal. However, if the radiation signal is provided (S11—Y), the radiation controller (152) can determine whether the degree of the shake determined by the shake determination unit (151) is equal to or more than the first threshold (S12).

And, if the determined degree of the shake is less than the first threshold (S12—N), the radiation controller (152) generates a radiation operation signal so that the radiation unit (110) can radiate the X-ray (S15).

However, if the determined degree of the shake is equal to or more than the first threshold at the time of receiving the radiation signal (S14-Y), the radiation controller (152) can delay the generation of the radiation operation signal (S14).

When the generation of the radiation operation signal is delayed, the radiation controller (152) determines that radiation delay time exceeds reference time (S15), and if the radiation delay time does not exceed the reference time (S15—N), the radiation controller (152) re-determines whether the radiation signal is provided (S11).

However, if the radiation delay time exceeds the reference time (S15-Y), the radiation controller (152) generates a preheat halt signal to prevent overheat of the filament so that the filament preheat of the radiation unit (110) can be halted.

Figure 7:
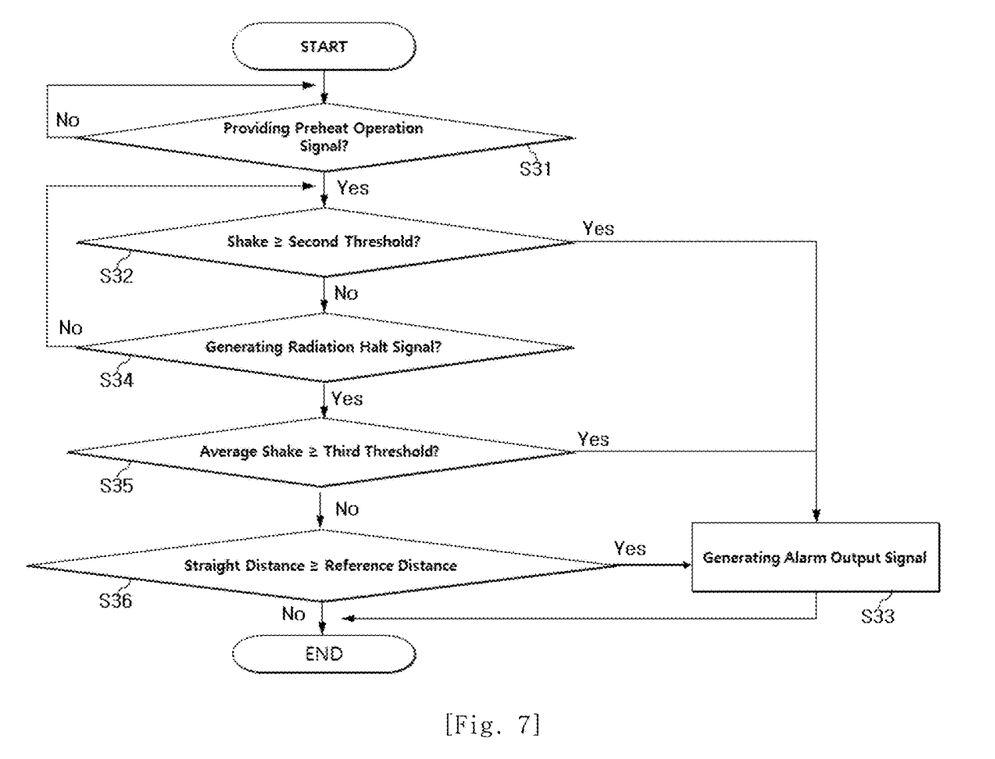
FIG. 7 is a flow chart for illustrating control operations of an alarm controller according to an embodiment of the present disclosure.

FIG. 7 is a flow chart for illustrating control operations of an alarm controller according to an embodiment of the present disclosure.

In the following descriptions, steps of generating an alarm output signal for controlling the warning alarm output unit (170) by the alarm controller (153) are described by referring to FIG. 7.

Firstly, the alarm controller (153) can determine whether a preheat operation signal is received from the radiation controller (152) (S31). If the preheat operation signal is not received (S31—N), the alarm controller (150) stands by until receiving the preheat operation signal. However, if the preheat operation signal is received (S31—N), the alarm controller (153) can determine whether the degree of the shake determined in real time by the shake determination unit (151) is equal to or more than a second threshold (S32).

If the degree of the shake determined in real time is equal to or more than the second threshold (S32—Y), the alarm controller (153) generates the alarm output signal (S33), but, if the degree of the shake determined in real time is less than the second threshold (S32—N), the alarm controller (153) can determine whether a radiation halt signal generated by the radiation controller (152) is received (S34). And, if the radiation halt signal is not received (S34—N), the alarm controller (153) continues to determine whether the degree of the shake is equal to or more than the second threshold until receiving the radiation halt signal, but, if the radiation halt signal is received (S34—Y), the alarm controller (153) calculates an average of the degree of the shake determined by the shake determination unit (151) from time of receiving the radiation operation signal from the radiation controller (152) to time of receiving the radiation halt signal from the radiation controller (152) and determines whether the calculated average is equal to or more than a third threshold (S35).

If the calculated average is equal to or more than the third threshold (S35—Y), the alarm controller (153) generates an alarm output signal (S33). However, if the calculated average is less than the third threshold (S35—N), the alarm controller (153) determines a separation or straight distance from a position where the X-ray radiation of the radiation unit (110) starts to a position where the radiation is completed, and determines whether the determined separation or straight distance is equal to or more than a reference distance (S36).

And, if the separation or straight distance is equal to or more than the reference distance (S36—Y), the alarm controller (153) generates the alarm output signal (S33), but, if the separation or straight distance is less than the reference distance (S36—N), the alarm controller (153) can terminate the control process of the warning alarm output unit (170) without generating the alarm output signal.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes. Accordingly, the scope of the disclosure is not to be limited by the above embodiments but by the claims and the equivalents thereof.

REFERENCE CHARACTERS OF DRAWINGS

10: Main Body
20: Manipulation Unit
110: Radiation Unit
130: Detection Unit
131: Shake Detection Sensor
133: Image Sensor
150: Controller
151: Radiation Controller
152: Shake Determination Unit
153: Alarm Controller
154: Position Determination Unit
155: Preheat State Determination Unit
156: Preheat Notification Controller
170: Warning Alarm Output Unit

What is claimed is:

1. An X-ray imaging device, comprising:
a radiation unit configured to preheat a filament and radiate an X-ray;
a detection unit configured to detect shake of the radiation unit and generate information on the shake of the radiation unit;
a controller configured to determine a degree of the shake based on the information on the shake received from the detection unit and control an operation of the radiation unit depending on the determined degree of the shake;
a warning alarm output unit configured to output a warning alarm; and
a manipulation unit configured to generate a radiation signal in response to manipulation of a user and provide the radiation signal to the controller,
wherein the controller comprises:
an alarm controller configured to, if an average of the degree of the shake determined while the radiation unit radiates the X-ray is equal to or more than a first threshold, generate an alarm output signal such that the warning alarm output unit outputs the warning alarm, and
a radiation controller configured to, if receiving the radiation signal, generate a radiation operation signal controlling the radiation unit to radiate the X-ray based on the degree of the shake,
wherein the radiation controller is configured to, if receiving the radiation signal, determine whether the degree of the shake is less than a second threshold, if the degree of the shake is less than the second threshold, generate the radiation operation signal, and, if the degree of the shake is equal to or more than the second threshold, halt generation of the radiation operation signal until the degree of the shake falls below the second threshold,
the manipulation unit is configured to generate a preheat signal in response to the manipulation of the user and provide the preheat signal to the radiation controller,
the radiation controller is configured to, if receiving the preheat signal, generate a preheat operation signal controlling to preheat a filament by the radiation unit, and if the providing of the preheat signal by the manipulation unit is halted or if time of halting generation of the radiation operation signal exceeds a reference time, generate a preheat halt signal controlling to halt preheat of the filament performed by the radiation unit.

2. The X-ray imaging device of claim 1,
wherein the alarm controller is configured to, if the degree of the shake is equal to or more than a third threshold, generate the alarm output signal.

3. The X-ray imaging device of claim 2, wherein
the controller further comprises a position determination unit configured to determine change in a position of the radiation unit based on information of a movement direction of the radiation unit and information of a movement distance of the radiation unit included in the information on the shake of the radiation unit, and
the alarm controller is configured to generate an alarm output signal based on the change in the position determined by the position determination unit.

4. The X-ray imaging device of claim 3, wherein the alarm controller is configured to, if a straight distance between a position of the radiation unit where X-ray radiation starts and a position of the radiation unit where the X-ray radiation ends is equal to or more than a reference distance, generate the alarm output signal.

* * * * *